July 1, 1952 M. J. WALTZ Plant Pat. 1,110
FUCHSIA PLANT
Filed Feb. 11, 1950
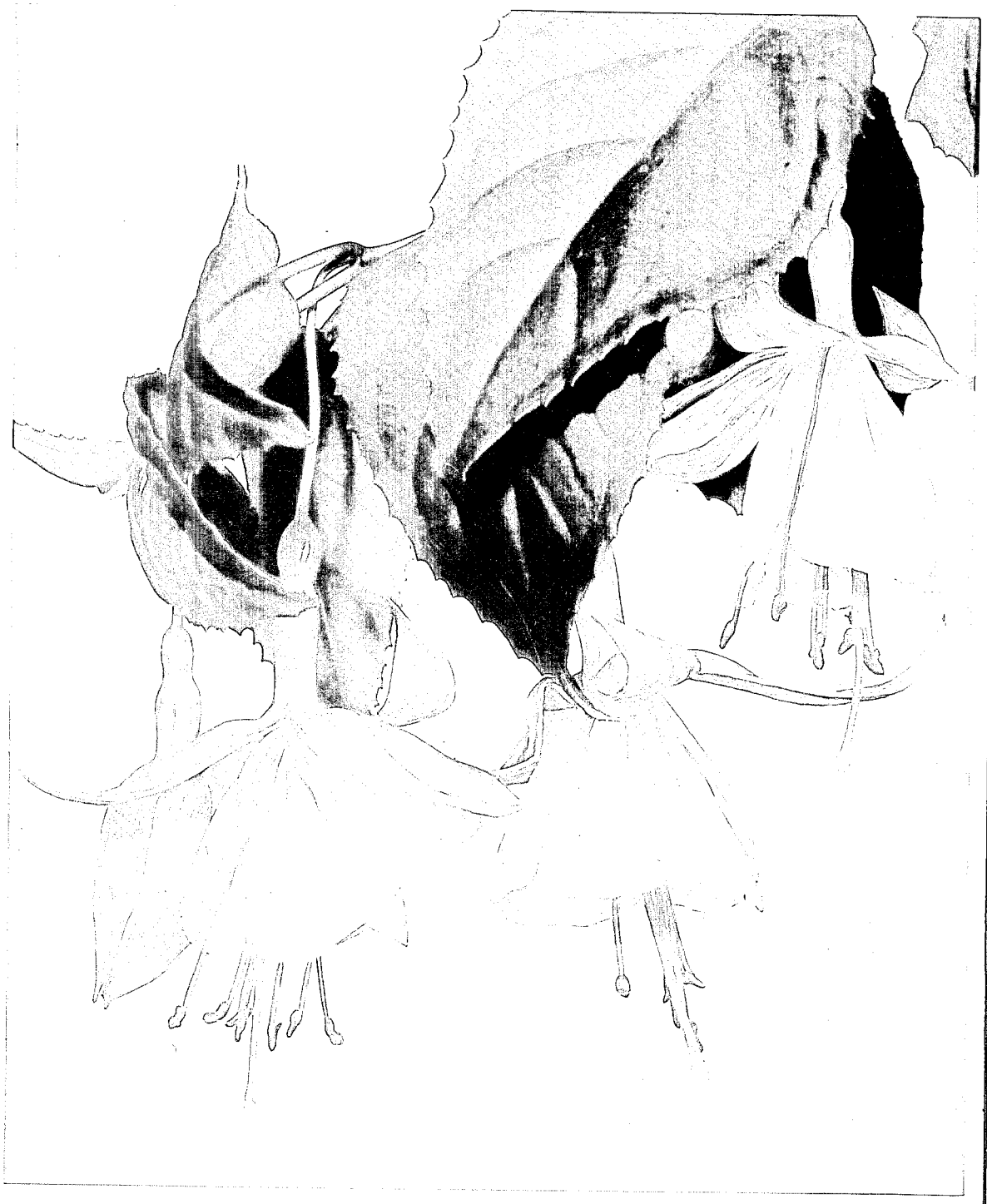
INVENTOR
MURIEL J. WALTZ
BY Harper Alden
ATTORNEY Patented July 1, 1952

Plant Pat. 1,110

UNITED STATES PATENT OFFICE 1,110

FUCHSIA PLANT

Muriel J. Waltz, Ross, Calif.

Application February 11, 1950, Serial No. 143,684

1 Claim. (Cl. 47—60)

This invention relates to a new and improved fuchsia plant, and more particularly to a fuchsia plant having fine growth characteristics and a new pink color of the flowers.

The plant was derived as a hybrid from the Mrs. G. G. Henry and Luckystrike strains (unpatented) of the late Gustav Neiderholzer. The fuchsia plant is characterized principally by the new deep pink coloring which has not previously been found in any fuchsia plant and has been asexually reproduced at Ross, Marin County, California, by cuttings which retained the characteristics of the parent fuchsia.

The plant is of a trailing variety and during growth continually throws out new branches from the roots, and the new branches are in turn self-branching forming a fine full basket with flowers both along the stem and at the tips of the branches. The blossom is single-flowered or semi-doubled-flowered. As a bud is of a carmine rose color (#621 Horticultural Color Chart) and as a flower is a clear bright phlox pink (#625/2 Horticultural Color Chart) which is intensified at the base of the petals.

In the accompanying drawings, the figure shows a typical branch tip including both a bud and fully opened blossoms, the drawing being shown at approximately actual size.

A detailed description of this new variety of fuchsia plant follows:

Habit of growth: Strong trailing variety which throws out branches from the roots and whose branches in turn are self-branching to form a full basket. Flowers occur both along the stem and at the tips of the branches.

Foliage: Medium sized, green leaves heavily veined, having serrated edges and evenly spaced along a branch. The leaves are of a general heart-shape except for being more distinctly pointed. Buds are long ovoid in shape being well pointed and having a color of carmine rose (#621 Horticultural Color Chart).

Flower: The flower is single or semi-double of medium or large size for the genus. The bell shaped corolla has overlapping and often pleated petals spreading at the tip of the flower. The flower is sturdy and takes the heat without wilting. The color is a clear bright phlox pink (#625/2 Horticultural Color Chart), deeper and more brilliant than previous shades of pink fuchsia. The flower matures well without losing its color. The stems are trailing and self-branching, the new growth being a deep rose shade maturing into green.

Ovary: Small, dark and green.

Tube: Medium size, slender tube having the same color as the bud.

Petals: From four to six large petals occur to each flower and petals over-lap and are often pleated giving a full effect. As the flower matures the petals flare open in bell-shaped fashion. The flowers are of a phlox pink as identified above and are slightly veined at the base of the flower.

Stamens: The stamens are long, approximately 2¾ inches in length, measured from the seed pod, and of a maroon color and terminate short of the long pistle, approximately 3 inches in length, measured from the seed pod, having a yellow tip which hangs well below the cluster of stamens.

Sepals: The four sepals are long, upturned, and pointed having the same color as the petals but of slightly deeper tone.

Parentage: Mrs. G. G. Henry and Luckystrike, both by Gustav Neiderholzer.

It will be realized that the foliage and flowers will vary somewhat with the seasons and growing conditions, however, the fuchsia plant is clearly differentiated from previous pink fuchsias by the deepness and exceptional character of its pink coloring.

I, therefore, point out and distinctly claim as my invention and discovery:

The new variety of pink fuchsia plant herein described and illustrated, characterized by the deepness and brilliance of the pink coloring of its flowers.

MURIEL J. WALTZ.

No references cited.